United States Patent
Chen et al.

(10) Patent No.: US 11,131,031 B2
(45) Date of Patent: Sep. 28, 2021

(54) HIGH-YIELD PREPARATION OF TWO-DIMENSIONAL COPPER NANOSHEETS

(71) Applicant: HONDA MOTOR CO., LTD., Tokyo (JP)

(72) Inventors: Shutang Chen, Powell, OH (US); Gugang Chen, Powell, OH (US)

(73) Assignee: HONDA MOTOR CO., LTD., Tokyo (JP)

( * ) Notice: Subject to any disclaimer, the term of this patent is extended or adjusted under 35 U.S.C. 154(b) by 466 days.

(21) Appl. No.: 16/006,673

(22) Filed: Jun. 12, 2018

(65) Prior Publication Data

US 2019/0376194 A1     Dec. 12, 2019

(51) Int. Cl.
*C25B 11/075*      (2021.01)
*C30B 29/02*      (2006.01)
(Continued)

(52) U.S. Cl.
CPC .............. *C25B 11/075* (2021.01); *B01J 37/16* (2013.01); *C01G 3/00* (2013.01); *C07C 1/12* (2013.01);
(Continued)

(58) Field of Classification Search
CPC ... C25B 11/0447; C25B 3/04; C25B 11/0405; C30B 7/14; C30B 29/64; C30B 29/02;
(Continued)

(56) References Cited

U.S. PATENT DOCUMENTS 7,829,059 B2   11/2010   Guo et al.
8,076,261 B2   12/2011   Hwang et al.
(Continued)

FOREIGN PATENT DOCUMENTS

CN   103112885 A    5/2013
CN   108127125 A * 6/2018
(Continued)

OTHER PUBLICATIONS

Shaik, A. H., and J. Chakraborty. "A simple room temperature fast reduction technique for preparation of a copper nanosheet powder." RSC advances 6.18 (2016): 14952-14957.*

(Continued)

*Primary Examiner* — Richard M Rump
(74) *Attorney, Agent, or Firm* — Arent Fox LLP (57) ABSTRACT

Cu-based nanostructures have excellent catalytic, electronic, and plasmonic performance due to their unique chemical and physical properties. A range of Cu materials including foil, spherical nanoparticles, nanowires, and nanocubes have been explored for catalyzing $CO_2$ electroreduction. However, practical application of the $CO_2$ electroreduction reaction requires Cu catalysts hold a high percentage of exposed surface atoms for improved product selectivity. The present disclosure describes a high temperature reduction method to prepare Cu nanosheets with size range from about 40 nm to about 13 μm in a hydrophobic system. The purity of trioctyphosphine (TOP) plays an important role for shape-controlled synthesis of Cu nanosheets. The morphology evolution was investigated by adjusting the feeding molar ratio of TOP/Cu-tetradecylamine complex. The Cu nanosheets formed by the methods of the present disclosure have high surface area and stability in solution for more than three months. These Cu nanosheets have applications in reducing $CO_2$ to fuels.

20 Claims, 10 Drawing Sheets

TOP: trioctylphosphine (51) Int. Cl.
| | |
|---|---|
| *C30B 29/64* | (2006.01) |
| *C07C 1/12* | (2006.01) |
| *C30B 7/14* | (2006.01) |
| *C01G 3/00* | (2006.01) |
| *B01J 37/16* | (2006.01) |
| *C22B 15/00* | (2006.01) |
| *C25B 3/25* | (2021.01) |
| *C25B 11/051* | (2021.01) |

(52) U.S. Cl.
CPC ............... *C22B 15/00* (2013.01); *C25B 3/25* (2021.01); *C25B 11/051* (2021.01); *C30B 7/14* (2013.01); *C30B 29/02* (2013.01); *C30B 29/64* (2013.01); *C07C 2523/72* (2013.01)

(58) Field of Classification Search
CPC ....... C30B 29/60; C07C 1/12; C07C 2523/72; B01J 23/72; C01G 3/00
See application file for complete search history.

(56) References Cited

U.S. PATENT DOCUMENTS

| | | |
|---|---|---|
| 8,178,585 B2 | 5/2012 | Petruska et al. |
| 9,751,071 B2 | 9/2017 | Kim et al. |
| 2008/0245186 A1 | 10/2008 | Yang et al. |
| 2011/0056564 A1 | 3/2011 | Korgel et al. |
| 2013/0220405 A1 | 8/2013 | Mahler et al. |
| 2013/0230717 A1 | 9/2013 | Xia et al. |
| 2014/0179941 A1 | 6/2014 | Bao |
| 2015/0147650 A1 | 5/2015 | Kovalenko et al. |

FOREIGN PATENT DOCUMENTS

| | | |
|---|---|---|
| KR | 10-2013-0114436 A | 10/2013 |
| WO | WO 2015/195650 A1 | 12/2015 |
| WO | WO 2016/049430 A1 | 3/2016 |
| WO | WO 2017/046268 A1 | 3/2017 |
| WO | WO 2017/091831 A1 | 6/2017 |

OTHER PUBLICATIONS

US 9,623,396, 4/2017, State of Oregon (withdrawn).
Fan Cui, et al., "Synthesis of Ultrathin Copper Nanowires Using Tris(trimethylsilyl)silane for High-Performance and Low-Haze Transparent Conductors", Nano Letters, vol. 15, pp. 7610-7615, 2015.
Hong-Jie Yang, et al., "Monodisperse Copper Nanocubes: Synthesis, Self-Asserribly, and Large-Area Dense-Packed Films", Chemistry of Materials, 26, pp. 1785-1793, 2014.
Jing Wang, et al., "The Synthesis and Tribological Characteristics of Triangular Copper Nanoplates as a Grease Additive", RSC Advances, vol. 7, pp. 40249-40254, 2017.
Shuling Xu, et al., "Selective synthesis of copper nanoplates and nanowires via a surfactant-assisted hydrothermal process", Materials Chemistry and Physics, vol. 120, pp. 1-5, 2010.
Shutang Chen, et al., "Anisotropic Seeded Growth of Cu—M (M=Au, Pt, or Pd) Bimetallic Nanorods with Tunable Optical and Catalytic Properties", Journal of Physical Chemistry, vol. 117, pp. 8924-8932, 2013.
Stafanos Mourdikoudis, et al., "Oleylamine in nanoparticle synthesis", Chem. Mater., 25, pp. 1465-1476, 2013.
Wenjia Luo, et al., "Facet Dependence of $CO_2$ Reduction Paths on Cu Electrodes", ACS Catalysis, vol. 6, pp. 219-229, 2016.
Yifan Li, et al., "Structure-Sensitive $CO_2$ Electroreduction to Hydrocarbons on Ultrathin 5-fold Twinned Copper Nanowires", Nano Letters, vol. 17, pp. 1312-1317, 2017.
Younan Xia, et al., "Shape-controlled Synthesis of Colloidal Metal Nanocrystals: Thermodynamic versus Kinetic Products", Journal of the America Chemical Society. vol. 137, pp. 7947-7966, 2015.
Anna Loiudice, et al., Tailoring Copper Nanocrystals towards C2 Products in Electrochemical CO2 Reduction:, Angewandte Chemie International Edition', vol. 55, pp. 5789-5792, 2016.
Fan Cui, et al., "Synthesis of Uitrathin Copper Nanowires Using Tris(trimethyisilyl)silane for High-Performance and Low-Haze Transparent Conductors", Nano Letters, vol. 15, pp. 7610-7615, 2015.
Hong-Jie Yang, et al., "Monodisperse Copper Nanocubes: Synthesis, Self-Assembly, and Large-Area Dense-Packed Films", Chemistry of Materials, 26, pp. 1785-1793, 2014.
Huizhang Guo, et al., Facile synthesis of Cu and Cu@Cu-Ni nanocubes and nanowires in hydrophobic solution in the presence of nickel and chloride ions+', Nanoscale, vol. 5, pp. 2394-2402, 2013.
Huizhang Guo, et al., "Shape-Selective Formation of Monodisperse Copper Nanospeheres and Nanocubes via Disproportionation Reaction Route and Their Optical Properties", Journal of Physical Chemistry C, vol. 118, pp. 9801-9808, 2014.
Hyo Sang Jeon, et al., "Prism-Shaped Cu Nanocatalysts for Electrochemical CO2 Reduction to Ethylene", ACS Catalysis, vol. 8, pp. 531-535, 2018.
Jing Wang, et al., "The Synthesis and Tribological Characteristics of Triangular Copper Nanoplates as a Grease Additive", RSC Advances, vol. 7, p. 40249-40254, 2017.
Lei Dai, et al., "Ultrastable Atomic Copper Nanosheets for Selective Electrochemical Reduction of Carbon Dioxide", Science Advances, vol. 3, 2017.
Manoj B. Gawande, et al., "Cu and Cu-Based Nanoparticles: Synthesis and Applications in Catalysis", Chemical Reviews, vol. 116, pp. 3722-3811, 2016.
Rulle Reske, et al., "Particle Size Effects in the Catalytic Electroreduction of CO2 on Cu Nanoparticles", Journal of the American Chemical Society, vol. 136, pp. 6978-6986, 2014.

\* cited by examiner

HIGH-YIELD PREPARATION OF TWO-DIMENSIONAL COPPER NANOSHEETS

TECHNICAL FIELD

The present disclosure is directed to copper nanoparticles, particularly copper nanosheets, methods of making the same, and catalytic applications of the same.

BACKGROUND

Shape-controlled synthesis of noble metal nanostructures has attracted extensive interest because of their structure-dependent catalytic, electronic, and optical properties. Compared to Au and Ag, Cu-based nanocatalysts have demonstrated excellent catalytic performance for $CO_2$ reduction reaction due to their lower working function and cost, and higher earth-abundancy. A series of Cu nanostructures have been explored for catalyzing $CO_2$ electroreduction, such as spheres, nanocubes, nanoprisms, and nanovires. Moreover, experimental results have shown that $CO_2$ electroreduction is sensitive to the surface morphology of Cu electrodes. Although Cu-based $Ni(OH)_2$ nanosheets with high percentage of surface area have demonstrated excellent catalytic efficiency and selectivity for $CO_2$ reduction reaction, the synthetic method of pure Cu nanosheets is not well established and the application of pure Cu nanosheets acting as electrocatalysts is rare in the literature. Thus, the development of efficient method for high yield preparation of two-dimensional Cu nanostructures becomes more and more important and urgent for converting $CO_2$ into fuels and chemicals.

In recent years, several reports have focused on the aqueous synthesis of Cu nanoparticles in disk-like shapes, for example, by the hydrothermal route, surfactant-assisted approach, and hard template method. However, these above methods are required to be carried out in aqueous solution and their size were more than a few micrometers. Moreover, their purity, stability, and yield of Cu nanosheets were very limited.

SUMMARY

The following presents a simplified summary of one or more aspects of the present disclosure in order to provide a basic understanding of such aspects. This summary is not an extensive overview of all contemplated aspects and is intended to neither identify key or critical elements of all aspects nor delineate the scope of any or all aspects. Its purpose is to present some concepts of one or more aspects in a simplified form as a prelude to the more detailed description that is presented later.

In some embodiments, the present disclosure is directed to a method of making a copper nanosheet, the method comprising: heating a reactant solution comprising a reducing agent and one or more surfactants to a temperature of about 280° C. to about 330° C., to form a heated solution; and injecting a hot solution of copper-containing precursor into the heated solution to form the copper nanosheet.

In some embodiments, the present disclosure is directed to a method of making a carbon dioxide conversion catalyst, the method comprising: heating a reactant solution comprising oleylamine and trioctylphosphine (TOP) to a temperature of about 280° C. to about 330° C., to form a heated solution; and injecting a hot solution of copper tetradecylamine (Cu-TDA) into the heated solution to form the copper nanosheet.

In some embodiments, the present disclosure is directed to a carbon dioxide reduction catalyst comprising a copper nanosheet characterized by a thickness of less than 100 nm; and a length of about 40 nm to about 13 μm.

These and other aspects of the invention will become more fully understood upon a review of the detailed description, which follows.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

The present disclosure is directed to a high temperature reduction method to prepare Cu nanosheets in a hydrophobic system at high temperature, using a thermal injection method. The purity of trioctylphosphine (TOP) plays an important role for the formation of sheet-like shape. The shape-evolution was investigated by adjusting the feeding molar ratio of trioctyphosphine/Cu-tetradecylamine complex. Using our method, large-scale synthesis of Cu nanosheets had been achieved and their size may be adjusted from about 40 nm to about 13 µm. Moreover, pure Cu nanosheets is stable in solution for more than three months. As a result of high percentage of surface area, these nanosheets will provide exciting new opportunities to study their plasmonic properties and enrich the choices of catalysts to convert $CO_2$ to fuels. In addition, the catalysts of the present disclosure are also usable under greener conditions. Furthermore, their excellent conductivity also endows Cu nanosheets' great potential in the fabrication of electronics.

As used herein, the term "about" is defined to being close to as understood by one of ordinary skill in the art. In one non-limiting embodiment, the term "about" is defined to be within 10%, preferably within 5%, more preferably within 1%, and most preferably within 0.5%.

Unless otherwise indicated, the purity of any reagents disclosed herein is up to and including the highest level commercially available or attainable using methods known to those of ordinary skill in the art.

In some embodiments, the present disclosure is directed to a method of making a copper nanosheet, the method comprising: heating a reactant solution comprising a reducing agent and one or more surfactants to a temperature of about 280° C. to about 330° C., to form a heated solution; and injecting a hot solution of copper-containing precursor into the heated solution to form the copper nanosheet. The reactant solution is suitably heated under inert conditions, i.e., in an inert atmosphere (e.g., Ar or $N_2$). The reaction temperature is limited by the boiling point of any liquid reagents and/or solvent(s) used in the method.

Reaction time will vary with temperature, and at a given temperature, longer reaction time results in larger nanosheets, but overreaction may give rise to aggregation. For example, at a reaction temperature of 300° C., the reaction time is suitably about 2 to about 90 minutes, and longer than 90 minutes of reaction time results in partial aggregation of the nanosheets. A 2-min reaction time results in smaller nanosheets, while a 90-min reaction time results in larger nanosheets. The average nanosheet size changed from 40 nm to 13 µm when the reaction time increased from 2 to 90 mins in a TOP (97%) system. At 330° C., 5 minutes of reaction results in nanosheets of average size 7.6 µm. At 280° C., 2 hours of reaction time results in nanosheets substantially free of aggregation. As used herein, the nanosheets are "substantially free of aggregation" if aggregation is present at a level of no more than 5%, preferably no more than 3%, more preferably no more than 2%, even more preferably no more than 1%, and most preferably no more than 0.5%. As will be known to those of ordinary skill in the art, heating to higher temperature will lower the reaction time needed to achieve a given point of reaction progress. At 300° C., 20 mins of reaction time may yield a larger nanosheet, with an average size of 8.9 µm with some aggregation. It is within the level of ordinary skill in the art to vary the reaction temperature and time to obtain the desired nanosheet size with the desired level of dispersion. In addition, reaction temperatures lower than about 280° C. may not permit sufficient reduction of the copper-containing precursor to permit formation of the nanosheets.

The reducing agent is suitably a $C_{16}$ to $C_{22}$ amine, such as a $C_{16}$ to $C_{18}$ amine. In some aspects, the reducing agent is oleylamine, hexadecylamine, or octadecylamine.

In some aspects, the reducing agent is oleylamine.

In some aspects, the one or more surfactants comprise trioctylphosphine (TOP).

In some aspects, the surfactant is TOP. TOP may be exposed to air or ambient conditions, or stored under inert conditions. Preferably, the TOP is stored under an inert atmosphere, such as in a glove box or dry box.

In some aspects, the one or more surfactants further comprise tetradecylamine (TDA). TDA (boiling point=289° C.) may require longer reaction time than TOP (boiling point=284-291° C.), depending on the size and/or dispersion level of nanosheets desired; suitable reaction time can be determined by those of ordinary skill in the art. The purity level of the TDA is suitably >96%, TOP and TDA may be mixed in any ratio, such as TOP:TDA 1:1, 2:1, 3:1, 5:1, 10:1, 15:1, 20:1, 1:2, 1:3, 1:4, 1:5, 1:10, or any ratio in between.

It has been discovered that the purity of TOP and the molar ratio of TOP to the copper-containing precursor (e.g., Cu-TDA) play important roles for formation of two-dimensional copper nanostructures, as will be discussed in greater detail below. Round and triangular copper nanosheets were synthesized using 90% and 97% pure TOP systems, respectively.

The purity of the TOP is suitably at least 90% or greater than 90%, such as at least or greater than: 91%, 92%, 93%, 94%, 95%, 96%, 97%, 98%, or 99%. In some aspects, the purity of the TOP is at least 97%.

In some aspects, the TOP is substantially free of trioctylphosphine oxide (TOPO). As will be known to persons of ordinary skill in the art, TOPO may form upon exposure of TOP to air. As used herein, the TOP is "substantially free of trioctylphosphine oxide" if the TOPO concentration is less than or equal to about 0.4 M, such as less than or equal to about 0.3 M, less than or equal to about 0.2 M, less than or equal to about 0.1 M, less than or equal to about 0.08 M, or any value or range in between.

In some aspects, the purity of the TOP is at least 90%.

In some aspects, the molar ratio of TOP to the copper-containing precursor is about 1.5:1 to about 2.8:1. In a 97% TOP system at 300° C., more than 90% of trigonal nanosheets are obtained at a molar ratio of 2.2:1 of TOP to Cu-TDA precursors with reaction time from 5 to 90 mins; while in a 90% TOP system at 300° C., a molar ratio of 2.2:1 of TOP to Cu-TDA precursors yields pure round nanosheets with reaction time from 20 to 120 mins.

In some aspects, the molar ratio of TOP to the copper-containing precursor is about 1.8:1 to about 2.8:1. Within this range of molar ratios, the reaction products are at least 90% copper nanosheets and the remainder is other copper nanoparticles when reacted at 300° C. for 20 mins.

In some aspects, the molar ratio of TOP to the copper-containing precursor is about 2.2:1.

The methods of the present disclosure are suitably conducted in high-boiling solvents/reagents, such as solvents/reagents boiling in the range of about 280° C. to about 330° C. In some aspects, the copper-containing precursor is dissolved in octadecene.

In some aspects, the reactant solution is heated to about 300° C.

Suitable copper-containing precursors include copper hexadecylamine (Cu-HDA), copper octadecylamine (Cu-ODA), copper tetradecylamine (Cu-TDA), or copper-dodecylamine (Cu-DDA). In some aspects, the copper-containing precursor is Cu-TDA. Stock solutions of Cu-TDA, Cu-HDA, Cu-ODA, or Cu-DDA can be prepared from reaction of copper (I) chloride and TDA, HDA, ODA, or DDA, respectively, under inert conditions. The TDA purity is suitably >96%. Stock solutions of Cu-TDA, Cu-HDA, Cu-ODA, or Cu-DDA can be prepared using methods known to those of ordinary skill in the art. In some aspects, copper nanosheets can be obtained using 5-30 ml oleylamine per 200 mg Cu-TDA.

The copper nanosheets produced according to the methods of the present disclosure range in size and thickness. The length of the trigonal nanosheets in a 97% TOP system ranges about 40 nm to about 13 μm, and the thickness ranges about 15 nm to about 500 nm. In a 90% TOP system, the length and thickness ranges of the round nanosheets are about 30 nm to about 200 nm and about 15 nm to about 50 nm, respectively.

Different sizes of the copper nanosheets have different applications. For example, copper nanosheets with thickness less than about 500 nm have been found to be reactive toward catalytic applications, such as carbon dioxide reduction, including reduction to methane. Without wishing to be bound to any particular theory, it is believed that smaller nanosheets have greater surface area which is beneficial for catalytic production of gases.

Particle size also affects the optical properties of the nanosheets, with larger nanosheets exhibiting redshifted absorption spectra. For example, nanosheets larger than about 1 μm have $\lambda_{max}$ at about 1000 nm, while nanosheets with size of less than about 500 nm have $\lambda_{max}$ at about 600 nm.

In some embodiments, the present disclosure is directed to a method of making a carbon dioxide conversion catalyst, the method comprising: heating a reactant solution comprising oleylamine and trioctylphosphine (TOP) to a temperature of about 280° C. to about 330° C., to form a heated solution; and injecting a hot solution of copper tetradecylamine (Cu-TDA) into the heated solution to form the copper nanosheet. All aspects of one method apply to the other with equal force.

In some aspects, the molar ratio of TOP to Cu-TDA is about 1.8:1 to about 2.8:1.

In some aspects, the molar ratio of TOP to Cu-TDA is about 2.2:1.

The purity of the TOP is suitably at least 90% or greater than 90%, such as at least or greater than: 91%, 92%, 93%, 94%, 95%, 96%, 97%, 98%, or 99%. In some aspects, the purity of the TOP is at least 97%.

In some aspects, the TOP is substantially free of trioctylphosphine oxide (TOPO).

In some aspects, the purity of the TOP is at least 90%.

In some embodiments, the present disclosure is directed to a carbon dioxide reduction catalyst comprising a copper nanosheet characterized by a thickness of less than 500 nm; and a length of about 40 nm to about 13 μm.

In some aspects, the present disclosure is directed to a method of generating methane, the method comprising reacting carbon dioxide with the carbon dioxide reduction catalyst comprising a copper nanosheet characterized by a thickness of less than 500 nm; and a length of about 40 nm to about 13 μm.

EXAMPLE 1

Experimental

Chemicals. Copper (I) chloride (99.99%), Copper (I) bromide (99.999%), Copper (II) chloride (99.99%), Copper (I) acetate (99.999%), Copper (II) acetylacetonate (99.9%), trioctylphosphine (TOP, 90%), trioctylphosphine (TOP, 97%), trioctylphosphine oxide (TOPO, 99%), oleylamine (OLA, 70%), oleylamine (OLA, 80~90%), hexadecylamine (HDA, 98%), octadecylamine (ODA), toluene (99.9%), acetone (99%), and chloroform (99.9%), 1-octadecene (ODE, 98%) were purchased from Sigma-Aldrich. Tetradecylamine (TDA, >96%) was purchased from TCI. Copper sulfate pentahydrate (99%) was purchased from ACROS ORGANICS. Hexane (99%), methanol (99%), and ethanol (200 proof) were purchase from Fisher Chemicals. All chemicals were used as received.

Synthesis of Cu-TDA precursor stock solution: 100 mg of copper (I) chloride, 200 mg of TDA, and 2 mL of ODE were added into the flask where oxygen was removed under Ar or $N_2$ flow. After Ar or $N_2$ blowing for 20 min, the mixed solution was heated to 190° C. on a hot plate and kept at this temperature for 30 min. During the heating process, TDA was melted at 38-40° C. and coordinated with Cu atoms to form Cu-TDA blue complex solution. The amounts of copper (I) chloride may vary from 50 mg to 300 mg, while the amounts of TDA, TOP, and oleylamine also increase proportionally. The stock solution could also be prepared by replacing TDA with HDA or ODA.

Synthesis of Cu nanosheets. 6.0 mL of OLA (70%) was loaded in a 25 mL three-neck flask where oxygen was removed through Ar blowing for 20 min. Then 1.0 mL of TOP (97%) were injected into the flask under Ar flow. After 20 min of Ar flowing, the flask was rapidly heated to 300° C. Next, 2 mL of Cu stock solution was quickly injected into the hot flask and the reaction solution turned to red immediately. The reaction was held at 300° C. for 20 min. Then the reaction mixture was naturally cooled to 100° C. and 5 mL of hexane (or another hydrophobic solvent such as toluene or chloroform) was injected. The products were separated by centrifuging at 2000 rpm for 2 min. The supernatant was discarded. A total of 10 mL of hexane (or another hydrophobic solvent such as toluene or chloroform) was then added to the sediment, and the mixture was centrifuged at 2000 rpm for 3 min. The washing procedure was repeated twice to remove unreacted precursors and surfactant. The Cu nanosheets were stored in a hydrophobic solvent (for example: hexane, toluene and chloroform) before characterization. The same amounts of TOP (97%) could be replaced with TOP (90%) or their mixture of TOP (97% and 90%). The Cu nanosheets could also be prepared by replacing OLA (70%) with OLA (80-90%), HDA, or ODA.

Characterization

The surface morphologies were investigated by a scanning electron microscope (QUANTA FEG 650) from FEI with a field emitter as the electron source. Elemental analysis was performed on an energy disperses spectroscopy (EDS) system equipped on the SEM. A Bruker D8 Advance X-ray diffractometer with Cu Kα radiation operated at a tube voltage of 40 kV and a current of 40 mA was used to obtain X-ray diffraction (XRD) patterns. Transmission electron microscopy (TEM) images were captured using an FEI Tecnai 20 microscope with an accelerating voltage of 200 kV. The surface composition of Cu nanosheets was detected by employing X-ray photoelectron spectroscopy (XPS, Kratos Axis). The instrument was equipped with both monochromated (Al) and dual (Mg and Al) x-ray guns. Calibration of the binding energy was carried out by calibrating the binding energy of the C 1 s peak to 284.6 eV.

Results and Discussion

Figure 1:
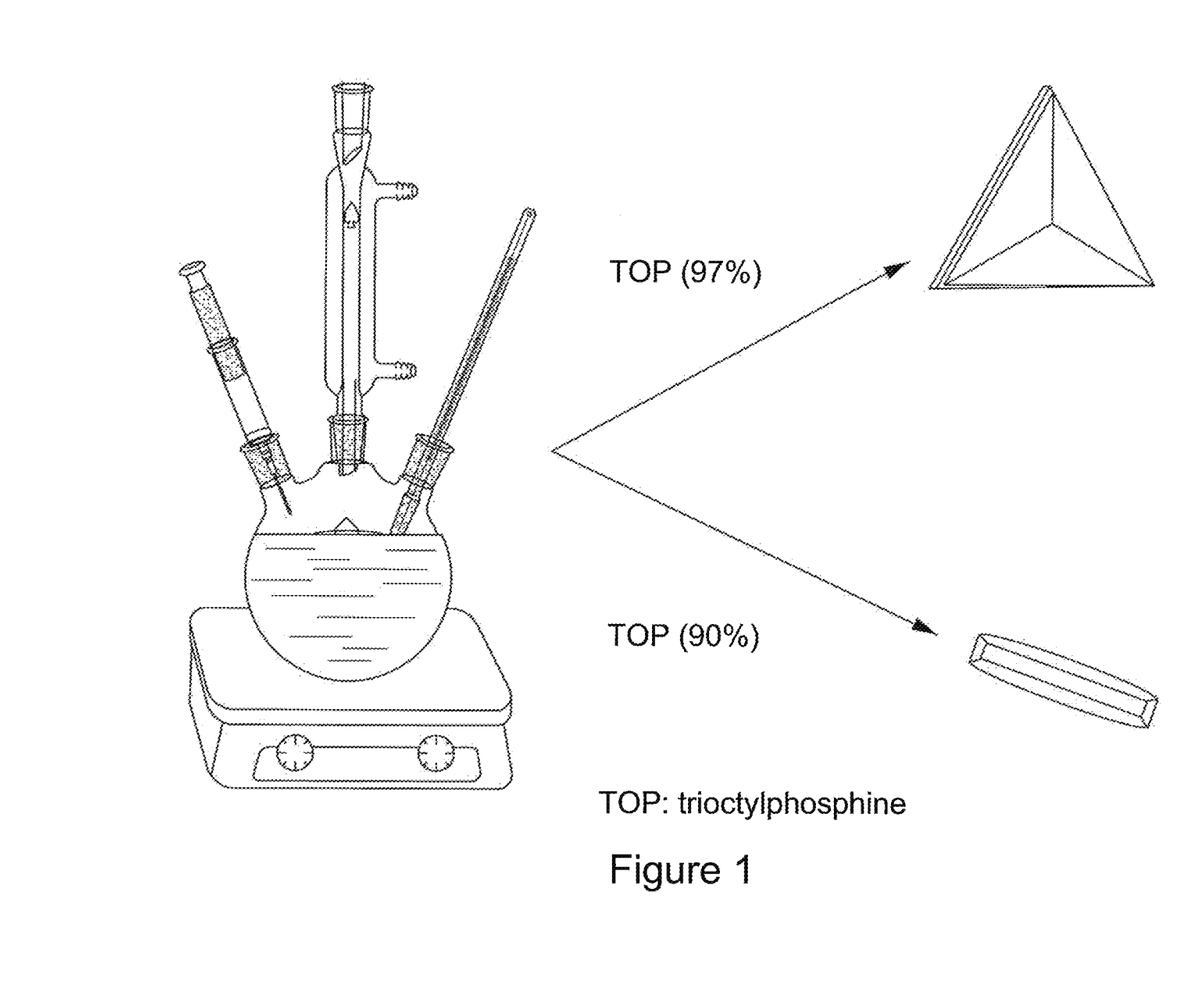
FIG. 1 shows an experimental scheme of shape-controlled synthesis of Cu nanosheets according to some aspects of the present disclosure.
Figure 2A:
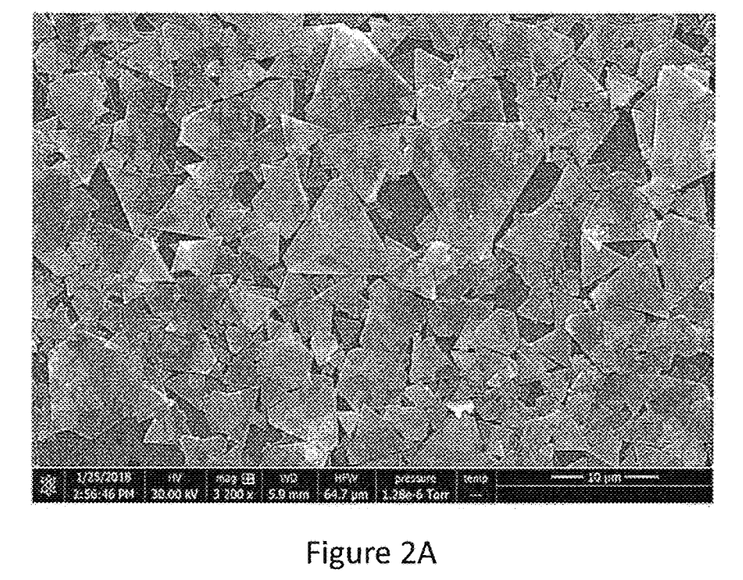
FIG. 2A shows a low resolution SEM image of Cu nanosheets prepared by adding 1.0 mL of 97% TOP according to some aspects of the present disclosure.
Figure 2B:
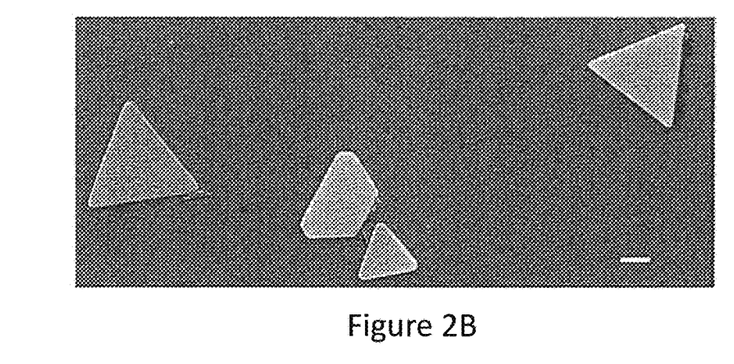
FIG. 2B shows a high resolution SEM image of Cu nanosheets prepared by adding 1.0 mL of 97% TOP according to some aspects of the present disclosure.
Figure 2C:
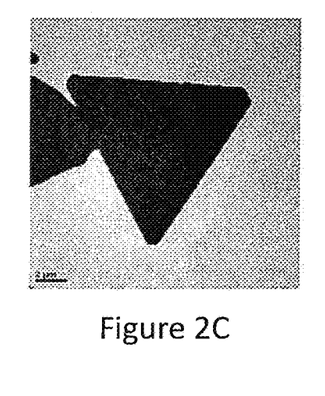
FIG. 2C shows a TEM image of Cu nanosheets prepared by adding 1.0 mL of 97% TOP according to some aspects of the present disclosure.
Figure 3A:
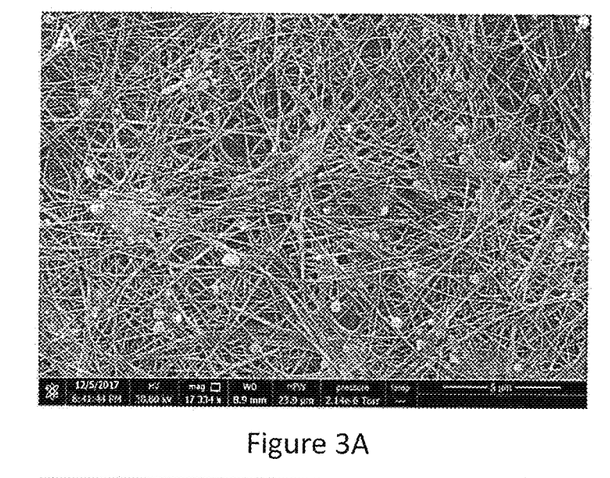
FIGS. 3A-3D show SEM images of Cu nanostructures prepared by adjusting the molar ratio of TOP (97%): Cu-TDA complex according to some aspects of the present disclosure: 0.4:1 (FIG. 3A), 1.8:1 (FIG. 3B), 2.8:1 (FIG. 3C), and 3.4:1 (FIG. 3D).
Figure 3B:
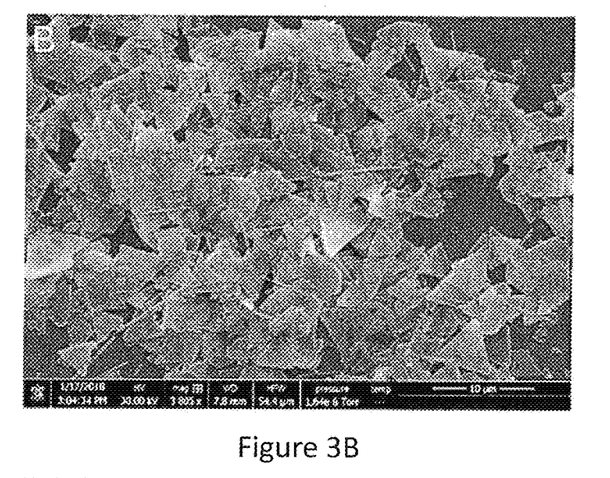
Figure 3C:
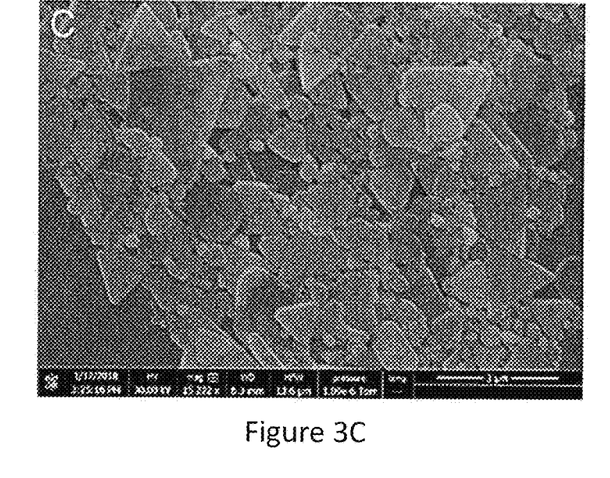
Figure 3D:
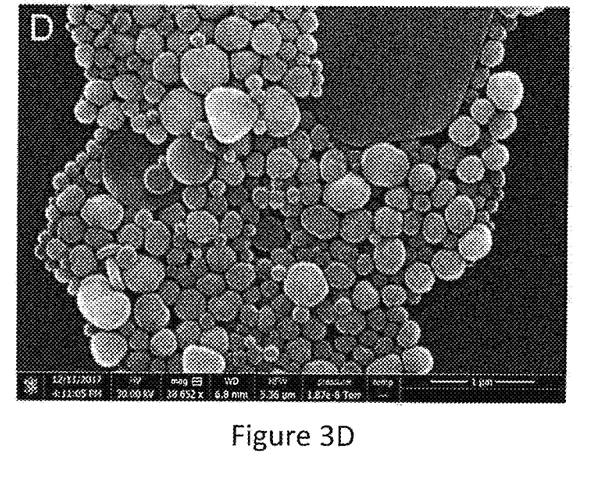

In our method, trioctylphosphine (TOP) with different purity was employed as shape-controlling ligand to synthesize Cu nanosheets. The round and triangular sheets were synthesized in 90% and 97% TOP systems, respectively, as shown in FIG. 1. Firstly, 97% TOP was chosen to act as the ligand, and we found the molar ratio of TOP to Cu-TDA complex was important to synthesize Cu nanosheets. When the molar ratio of TOP to Cu-TDA complex is 2.2:1, the reaction solution turned to red immediately after injecting copper precursor at 300° C. FIGS. 2A-C showed the majority of products were triangular sheets, and less than 10% sheets were polygon. The size range of sheets was between a few hundred nanometers to fifteen micrometers. One-dimensional Cu nanowires were prepared at the lowest molar ratio of 0.4, as shown in FIG. 3A. Although TOP has a strong coordinating ability with copper crystal, the shape of Cu nanostructures is determined by oleylamine because of the lower concentration of TOP. The growth mechanism was confirmed by recent studies due to the weak interaction of alkylamines with Cu {110} facets. See F. Cui, Y. Yu, L. Dou, J. Sun, Q. Yang, C. Schildknecht, K. Schierle-Arndt and P. Yang, "Synthesis of Ultrathin Copper Nanowires Using Tris(trimethylsilyl)silane High-Performance and Low-Haze Transparent Conductors", Nano Letters, Vol. 15, 7610-7615, 2015, which is incorporated herein by reference in its entirety. After increasing the molar ratio to 1.8:1, two-dimensional Cu nanosheets were dominant of the products (FIG. 3B), which indicated TOP restricted the preferential growth of Cu {110} facets. More than 90% of Cu triangular nanosheets were obtained at the molar ratio of 2.2 (FIG. 2A-C). With further increasing of molar ratio of TOP (97%) to Cu-TDA complex, Cu polyhedral nanoparticles appeared (2.8) and then dominated the products (3.4). Thus, pure Cu triangular nanosheets may be synthesized by optimizing the molar ratio of the surfactant and precursors.

Figure 4A:
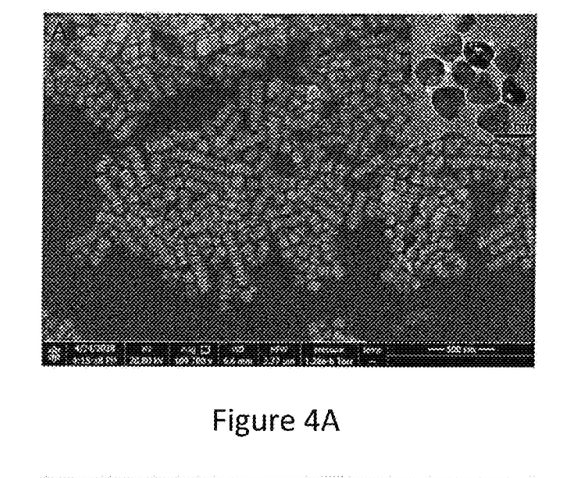
FIGS. 4A-4D show SEM images of Cu nanosheets prepared at different reaction intervals by adding 1.0 mL of 90% TOP according to some aspects of the present disclosure: 20 min (FIG. 4A), 40 min (FIG. 4B), 60 min (FIG. 4C), and 120 min (FIG. 4D). The inserts are the corresponding TEM images.
Figure 4B:
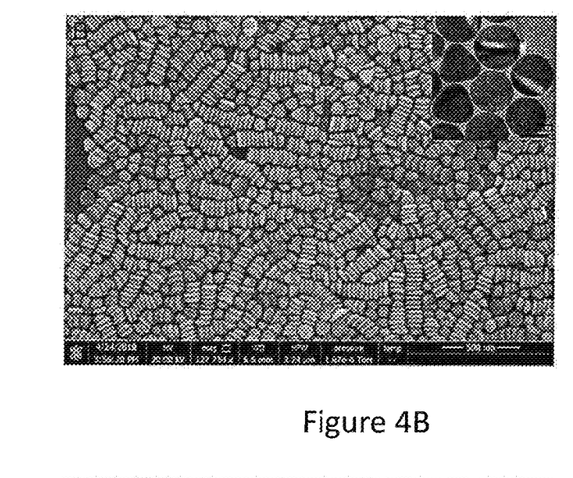
Figure 4C:
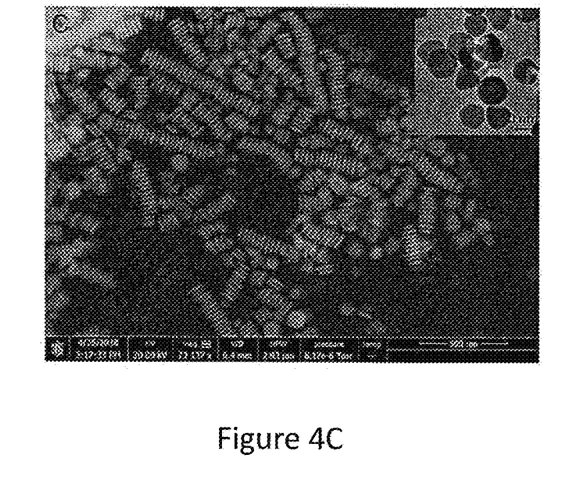
Figure 4D:
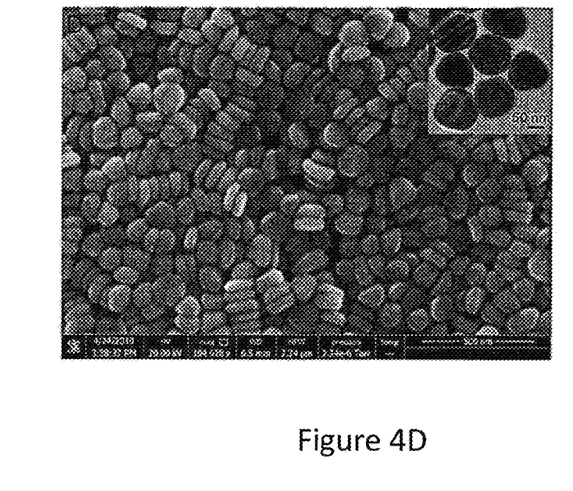
Figure 5A:
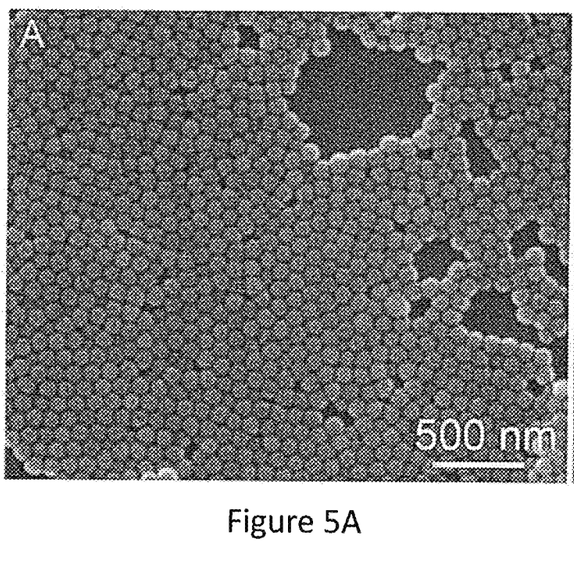
FIG. 5A shows an SEM image of quasi-cube nanocrystals prepared by employing TOP (97%, exposed to air one week).
Figure 5B:
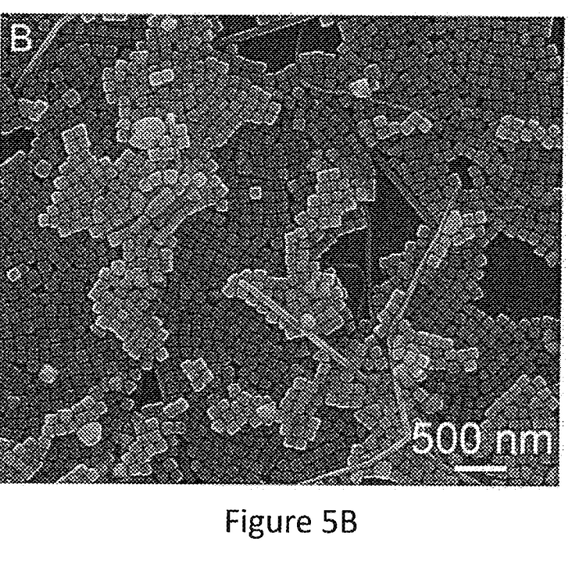
FIG. 5B shows an SEM image of Cu nanocubes prepared by adding 200 mg of TOPO to 97% TOP that was not exposed to air.

A previous study reported Cu nanocubes were prepared in TOP (90%) and oleylamine systems at 330° C. See H. Yang, S. He, H. Chen and H. Yuan, "Monodisperse Copper Nanocubes: Synthesis, Self-Assembly, and Large-Area Dense-Packed Films", Chemistry of Materials, Vol. 26, 1785-1793, 2014, which is incorporated herein by reference in its entirety. When employing TOP (90%) in our method, reaction solution turned to red after injecting copper precursor solution and reacting for 3 min due to the effect of the purity of TOP on reaction thermal dynamics. Round thinner Cu nanosheets were synthesized after prolonging reaction to 20 min (FIG. 4A), which indicated the purity of TOP has a vital effect on shape-controlled synthesis of Cu nanosheets. When extending the reaction time to 120 min, the average diameter and the thickness of nanosheets increased from 40 nm to 190 nm and from 15 nm to 37 nm, respectively, as shown in FIG. 4C-D. It is well known that TOP is sensitive to air which can be easily oxidized to form trioctylphosphine oxide (TOPO). When fresh TOP (97%) had been exposed to air for more than one week, or additional TOPO was mixed in TOP (97%), Cu nanocubes were synthesized following our method due to the presence of TOPO, as shown in FIGS. 5A-B, respectively. Similar studies had been reported to prepare copper nanocubes by employing TOPO as ligand. See H. Guo, Y. Chen, M. B. Cortie, X. Liu, Q. Xie, X. Wang and D. Peng, "Shape-Selective Formation of Monodisperse Copper Nanospheres and Nanocubes via Disproportionation Reaction Route and Their Optical Properties", Journal of Physical Chemistry C, Vol. 118, 9801-9808, 2014, which is incorporated herein by reference in its entirety. Thus, the present disclosure emphasizes that fresh TOP plays an important role for the formation of Cu nanosheets.

Figure 6A:
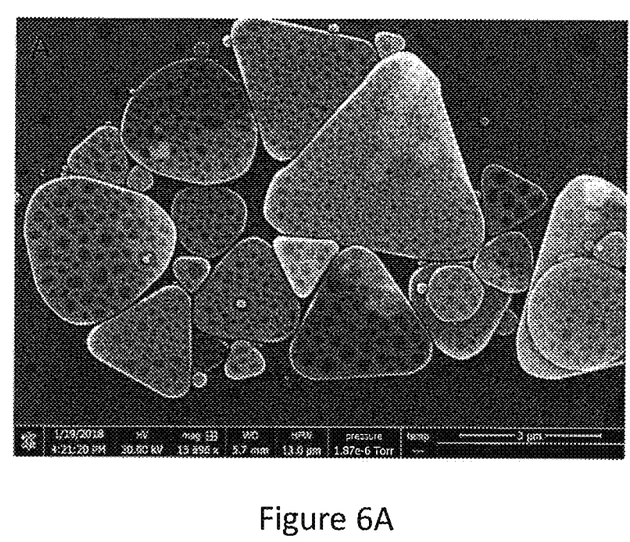
FIGS. 6A and 6B show SEM images of Cu nanosheets prepared by injecting CuBr-TDA precursors in different purities of TOP according to some aspects of the present disclosure: 97% TOP for reaction 20 min (FIG. 6A), and 90% TOP for 60 min (FIG. 6B).
Figure 6B:
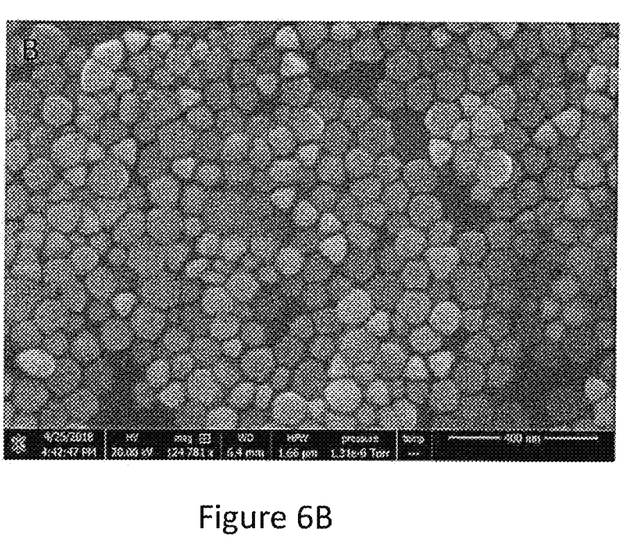

Besides the purity of TOP, the molar ratio of TOP (97%) to Cu-TDA complex, reaction time, and the type of copper precursors also play an important role for the formation of Cu nanosheets. The reaction conditions were kept identical to the Cu nanosheets synthesis, only copper stock solution were prepared by replacing copper (I) chloride with copper (I) bromide. FIGS. 6A-B indicated sheet-shape Cu nanostructures were synthesized by employing copper bromide in different TOP systems. Triangular Cu nanosheets with a size range from 500 nm to 4 µm were prepared in TOP (97%), while polygon Cu nanosheets with an average thickness of 25 nm and the size of 68 nm were prepared in TOP (90%) systems, respectively, which was similar to that using copper (I) chloride as the stock solution precursor. Besides copper (I) chloride and copper (I) bromide, Cu nanosheets were also synthesized when employing copper (I) acetate or copper (II) sulfate pentahydrate as precursors. However, no sheet shape was found when replacing copper (I) chloride with copper (II) acetylacetonate or copper (II) chloride due to their differences of the nucleation and growth rate.

Figure 7:
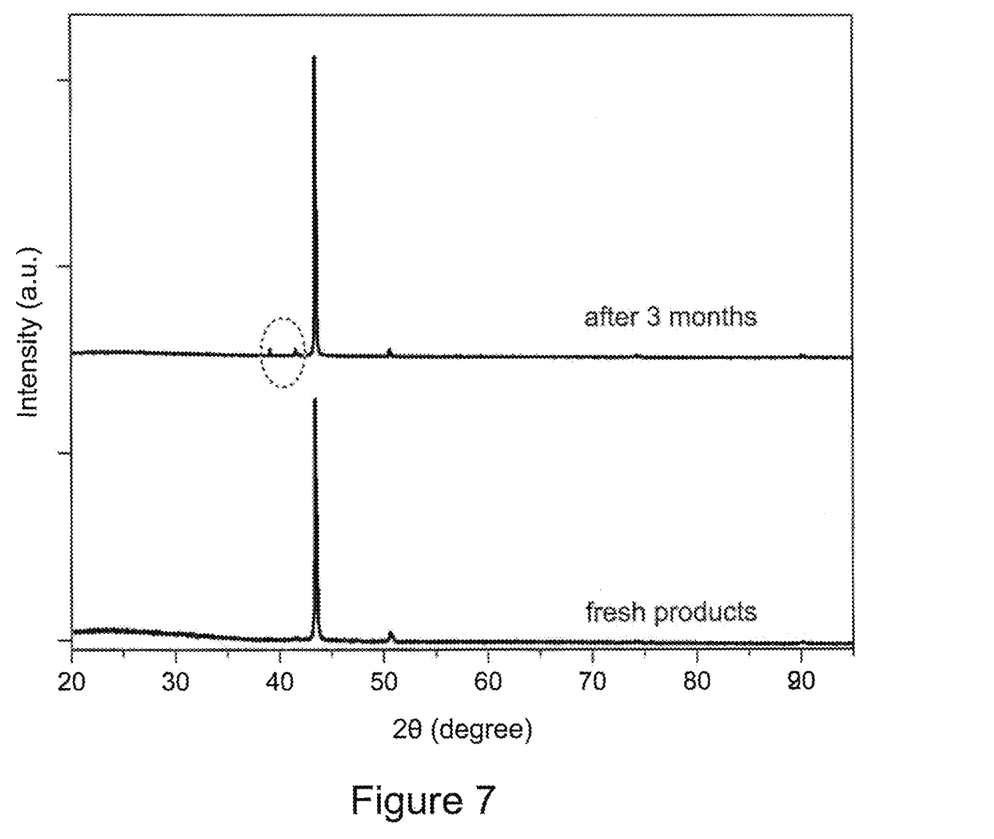
FIG. 7 shows XRD patterns of Cu nanosheets prepared according to some aspects of the present disclosure stored in hexane for more than 3 months.
Figure 8:
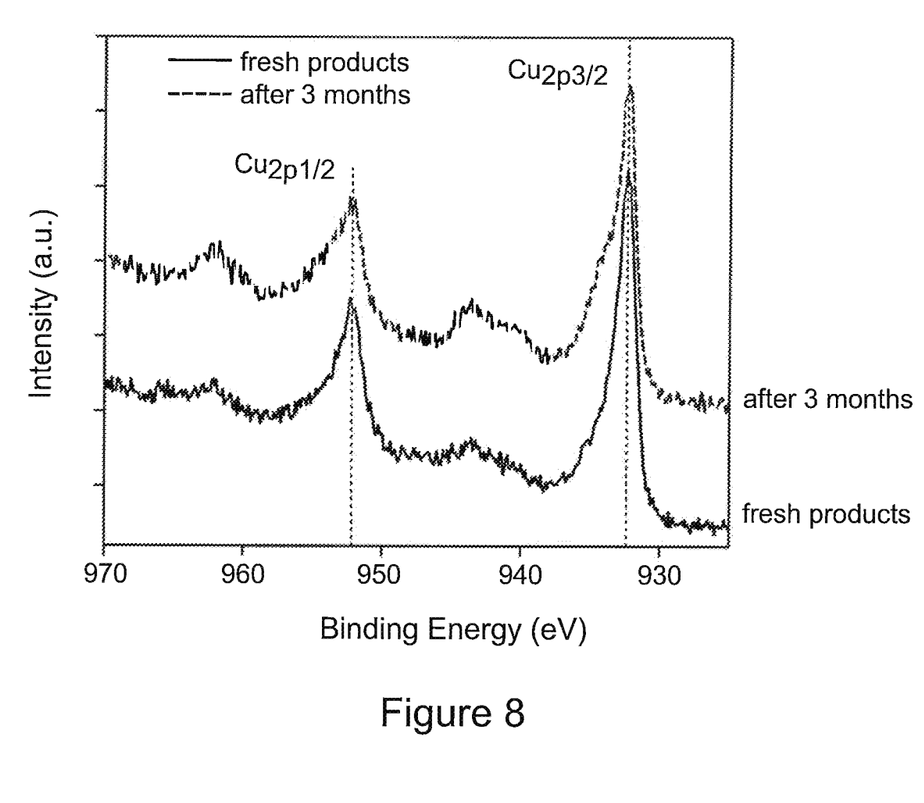
FIG. 8 shows XPS spectra of $Cu_{2p}$ with Cu nanosheets prepared according to some aspects of the present disclosure stored in hexane for more than 3 months.

Because Cu nanostructures can be easily oxidized in air, the stability of Cu nanosheets will affect their surface property and determine their further application. X-ray diffraction technique was employed to study the stability of Cu triangular nanosheets stored in hexane solution, as shown in FIG. 7. Cu nanosheets has the strongest {111} diffraction peak, which is very different from that of fcc bulk Cu (JPCDS 04-0836) See S. Chen, S. Jenkins, J. Tao, Y. Zhu, and J. Chen, "Anisotropic seeded growth of Cu-M (M=Au, Pt, or Pd) bimetallic nanorods with tunable optical and catalytic properties, the Journal of Physical Chemistry C, Vol. 117, 8924-8932, 2013, which is incorporated herein by reference in its entirety. Here we should emphasize the XRD sample was prepared by drying Cu nanosheets solution on a glass slide at room temperature. As a result, almost all of the Cu nanosheets have a preferred orientation with {111} facets parallel to the glass substrate. Compared to the XRD pattern of fresh Cu nanosheets, no obvious phase change had been found after storing products in hexane for more than three months. Although weaker peaks of copper oxide were found, the amount of surface oxidation of Cu nanosheets may be negligible. The surface composition of Cu nanosheets was further detected by X-ray photoelectron spectroscopy (XPS) technique. FIG. 8 showed XPS spectra of the $Cu_{2p}$ of Cu nanosheets. The strong peaks at ~932.8 and 952.5 eV could be ascribed to the binding energies of the 2p3/2 and 2p1/2 electrons of Cu. Note that very weaker peak from Cu (II) (940~950 eV) had been observed after three months, which is consist with XRD analysis. Thus, Cu nanosheets synthesized with the methods of the present disclosure are stable and can be utilized for further applications.

Conclusion

To summarize, Cu nanosheets had been obtained in hydrophobic phase by hot-injection method at 300° C. The SEM results indicated the purity of TOP and the molar ratio of TOP/Cu-TDA played important roles for the formation of two-dimensional Cu nanostructures. Using our current method, the size and the thickness of Cu nanosheets may be controlled from 40 nm to 13 μm and from 15 nm to 500 nm, respectively. The XRD and XPS studies showed Cu nanosheets were stable when stored in hydrophobic solvents. As a result of high percentage of surface area, these Cu nanosheets can provide potential applications in electronics, catalysis, and optical devices.

EXAMPLE 2

Instruments for Catalytic Experiment

Gas chromatograph (GC 17A, SHIMADZU) was employed to analyze the concentration of gas products. Liquid products were analyzed by high-performance liquid chromatograph (HPLC, Dionex UltiMate 3000; UHPLC+, Thermo Scientific).

Electrochemical Measurement

Electrochemical $CO_2$ reduction experiments were conducted using a potentiostat (VersaSTAT MC) in a two-compartment electrochemical cell separated by an anion-exchange membrane (Selemion AMV). A platinum plate counter electrode and a leak-free Ag/AgCl reference electrode (innovative Instruments, diameter: 2.0 mm) were used in a three-electrode configuration. Working electrodes were prepared by drop-casting 1.0 μg of Cu or Cu trigonal nanosheets (average size: 8.9 μm, dispersed in hexanes) onto a carbon glassy electrode (Alfa Aesar: diameter of 1.0 cm$^2$) and drying under argon at room temperature. The working electrode and the counter electrode compartments held 2.0 mL of electrolyte each, and the working compartment was sealed in order to allow measurements of gas products. All potentials in this work are converted to the RHE scale by E(vs RHE)=E(vs Ag/AgCl)+0.205 V+0.0591×pH. The 0.1 M $KHCO_3$ electrolyte was prepared from $K_2CO_3$ saturated with $CO_2$ (pH 7.5).

During electrochemistry, $CO_2$ flowed through the working compartment at a rate of 5 sccm. During chronoamperometry, effluent gas from the cell went through the sampling loop of a GC to analyze the concentration of gas products. Quantification of the products was performed with the conversion factor derived from the standard calibration gases. Liquid products were analyzed afterward by HPLC. The concentrations are calculated through the software and are based on calibration curves which we developed for each individual component. Faradaic efficiencies were calculated from the amount of charge passed to produce each product, divided by the total charge passed at a specific time or during the overall run.

Discussion and Catalytic Results

Figure 9:
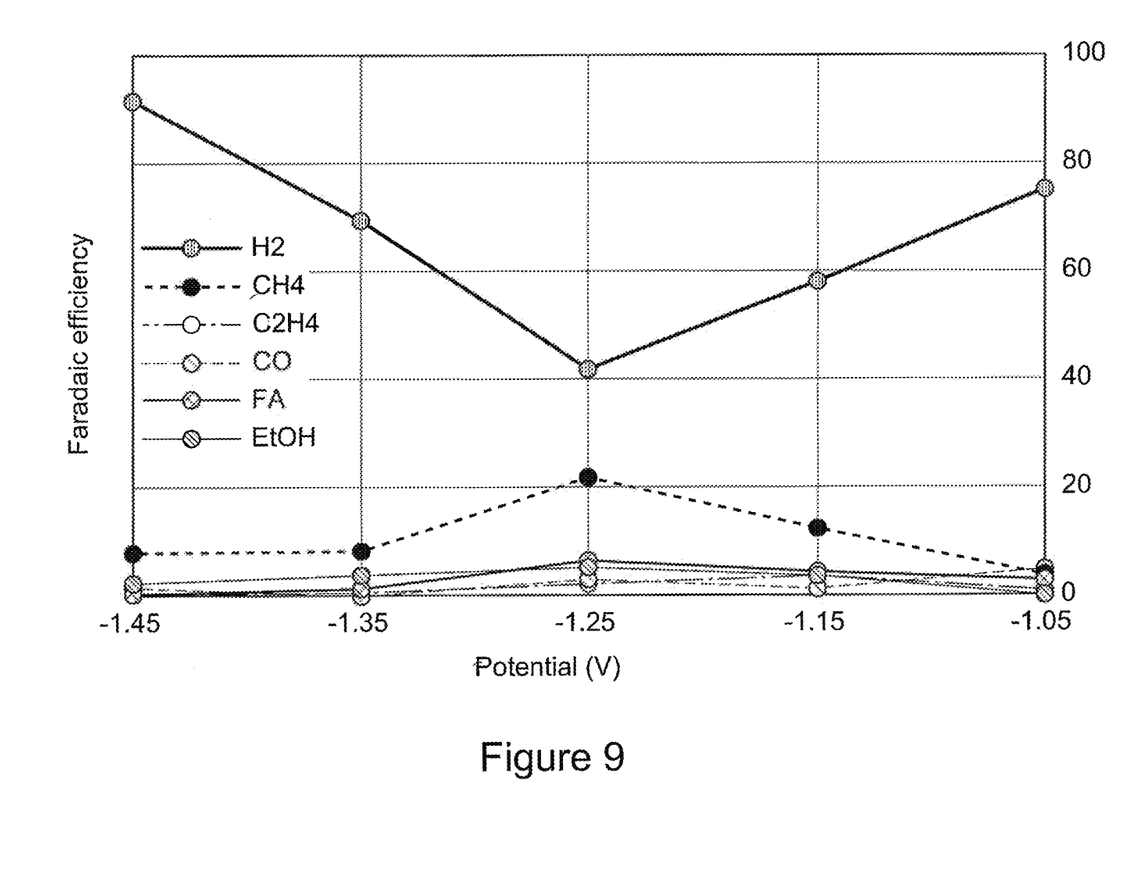
FIG. 9 shows the Faradaic efficiency for various products formed upon $CO_2$ reduction catalyzed by Cu nanosheets according to some aspects of the present disclosure.

Systematic $CO_2$ reduction reactions have been carried out for 2.5 h on Cu trigonal nanosheets with an average size of 8.9 μm under potentiostatic conditions in the potential range from −1.05 V to −1.45 V vs reversible hydrogen electrode (RHE). There are visible differences in the potential-dependent product distributions as demonstrated by the Faradaic efficiency (FE) plots in FIG. 9 (FA, formic acid). Faradaic efficiency for each product as a function of potential is shown in FIG. 9 for major and minor products. Cu trigonal nanosheets with an average size of 8.9 μm are employed as the catalysts for $CO_2$ reduction reaction. The scanning potential is relative to reversible hydrogen electrode (RHE).

A first remarkable difference concerns the FEs of hydrogen production which are significantly lower at −1.25 V vs RHE. $FE_{H2}$ values gradually drop down from 75.3% at −1.05 V to 42.1% at −1.25 V, and then increase to 91.7 at −1.45 V. Another difference is $FE_{CH4}$ values which gradually increase from 3.6% at −1.05 V to 21.7% at −1.25 V, and then decrease to 7.8% at −1.45 V. Based on the above analytical results, Cu trigonal nanosheets as the catalysts for $CO_2$ reduction reaction are selective to $CH_4$ product at −1.25 V relative to RHE. Our XRD results (FIG. 7) have demonstrated the surface facet of Cu trigonal nanosheets is {111}. Recent calculation studies show Cu {111} favors COH* formation, through which methane and ethylene are produced via a common $CH_2$ species under high overpotential. See W. Luo, X. Nie, M. Janik and A. Asthagiri, "Facet dependence of $CO_2$ reduction paths on Cu electrodes," ACS Catalysis, Vol 6, 219-229, 2016, which is hereby incorporated by reference herein in its entirety. Thus, the product selectivity of Cu trigonal nanosheets with exposed large area of {111} as catalysts for $CO_2$ reduction reaction is consistent with theoretical calculation.

Figure 10:
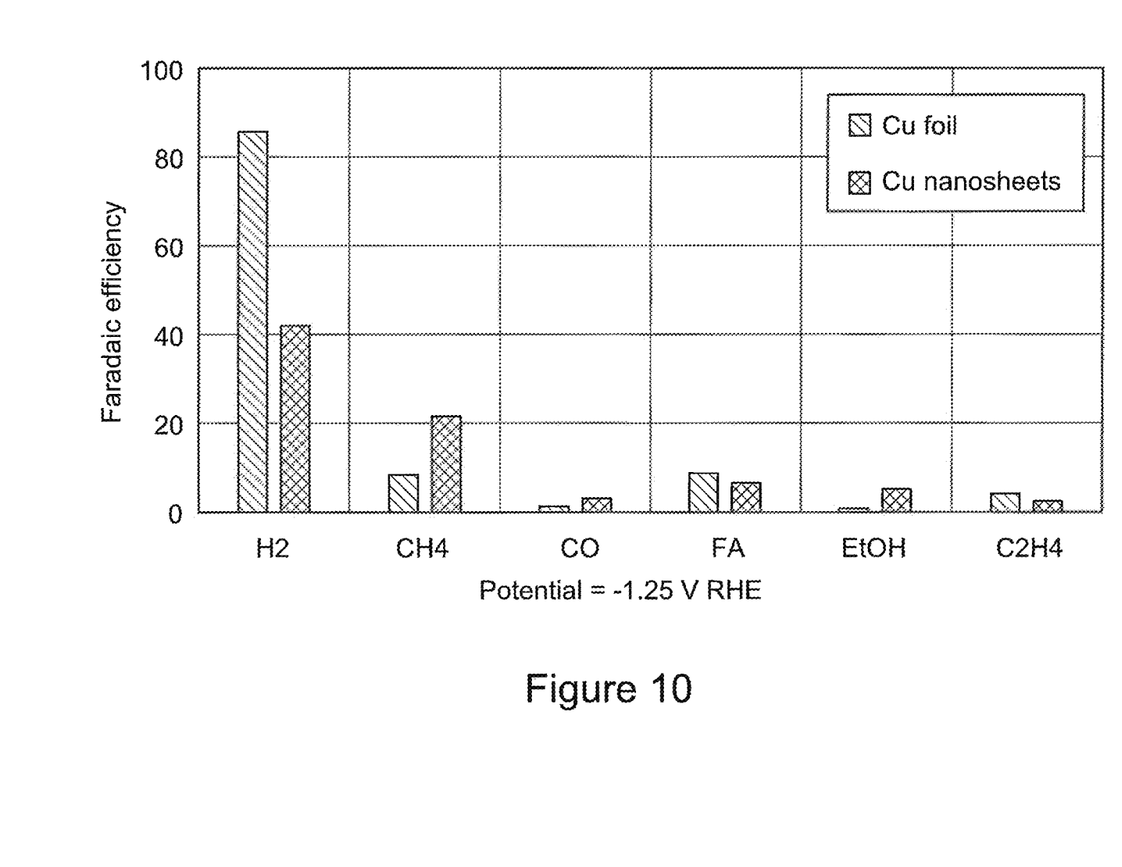
FIG. 10 shows the Faradaic efficiencies of the hydrogen evolution reaction and $CO_2$ reduction reaction products as derived from standard Cu foil and from Cu nanosheets according to some aspects of the present disclosure.

The difference in product selectivity can be affected by the surface facet of Cu catalysts. We could confirm that Cu trigonal nanosheets had higher FE of $CH_4$ product than that of bulk Cu foil (FIG. 10). The selectivity to $CH_4$ is surprising. Although Cu {111} is understood to favor $C_1$ products (e.g., $CH_4$, CO, HCHO, HCOOH) (see, e.g., "Facet dependence of $CO_2$ reduction paths on Cu electrodes," ACS Catalysis, Vol 6, 219-229, 2016), no specific selectivity to $CH_4$ had been predicted. The present experimental result showing selectivity to $CH_4$ higher than other $C_1$ products is surprising. As shown in FIG. 10, the Faradaic efficiencies (FEs) of the hydrogen evolution reaction/$CO_2$ reduction reaction products as derived from standard Cu foil and Cu trigonal nanosheets with an average size of 8.9 μm as the catalysts. The scanning potential is −1.25 V relative to reversible hydrogen electrode (RHE). The hydrogen evolution reaction (HER) competes with $CO_2$ reduction reaction in our catalytic experiments. At a potential of −1.25 V vs RHE, the $FE_{H2}$ value of bulk Cu foil is almost twice that of Cu trigonal nanosheets, while $FE_{CH4}$ of Cu trigonal nanosheets is 2.5 times larger than that of bulk Cu foil. The higher percentage of {111} surface of Cu trigonal nanosheets could not only improve the selectivity for $CH_4$ production, but also slow down the HER. The selectivity to $CH_4$ is surprising or unexpected. The catalytic activity and selectivity are also dependent on the catalysts' size and shape. Generally, normalized catalytic activity increases with decreasing catalyst size. Further experiments to verify this effect are underway.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference. Moreover, nothing disclosed herein is intended to be dedicated to the public.

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C.

Moreover, all references throughout this application, for example patent documents including issued or granted patents or equivalents; patent application publications; and non-patent literature documents or other source material are hereby incorporated by reference herein in their entireties, as though individually incorporated by reference.

The foregoing description of various aspects and examples have been presented for purposes of illustration and description. It is not intended to be exhaustive nor to limit the disclosure to the forms described. The embodiment(s) illustrated in the figures can, in some instances, be understood to be shown to scale for illustrative purposes. Numerous modifications are possible in light of the above teachings, including a combination of the abovementioned aspects. Some of those modifications have been discussed and others will be understood by those skilled in the art. The various aspects were chosen and described in order to best illustrate the principles of the present disclosure and various aspects as are suited to the particular use contemplated. The scope of the present disclosure is, of course, not limited to the examples or aspects set forth herein, but can be employed in any number of applications and equivalent devices by those of ordinary skill in the art. Rather, it is hereby intended the scope be defined by the claims appended hereto.

What is claimed is:

1. A method of making a copper nanosheet, the method comprising:
   heating a reactant solution comprising a reducing agent and one or more surfactants to a temperature of about 280° C. to about 330° C., to form a heated solution; and
   injecting a hot solution of copper-containing precursor into the heated solution to form the copper nanosheet.

2. The method of claim 1, wherein the reducing agent is oleylamine, hexadecylamine, or octadecylamine.

3. The method of claim 2, wherein the reducing agent is oleylamine.

4. The method of claim 1, wherein the one or more surfactants comprise trioctylphosphine (TOP).

5. The method of claim 4, wherein the one or more surfactants further comprise tetradecylamine (TDA).

6. The method of claim 4, wherein the purity of the TOP is at least 97%.

7. The method of claim 6, wherein the TOP is substantially free of trioctylphosphine oxide (TOPO).

8. The method of claim 4, wherein the purity of the TOP is at least 90%.

9. The method of claim 4, wherein the molar ratio of TOP to the copper-containing precursor is about 1.5:1 to about 2.8:1.

10. The method of claim 9, wherein the molar ratio of TOP to the copper-containing precursor is about 1.8:1 to about 2.8:1.

11. The method of claim 9, wherein the molar ratio of TOP to the copper-containing precursor is about 2.2:1.

12. The method of claim 1, wherein the copper-containing precursor is dissolved in octadecene or squalene.

13. The method of claim 1, wherein the reactant solution is heated to about 300° C.

14. The method of claim 1, wherein the copper-containing precursor is copper tetradecylamine (Cu-TDA).

15. A method of making a carbon dioxide conversion catalyst comprising a copper nanosheet, the method comprising:
   heating a reactant solution comprising oleylamine and trioctylphosphine (TOP) to a temperature of about 280° C. to about 330° C., to form a heated solution; and
   injecting a hot solution of copper tetradecylamine (Cu-TDA) into the heated solution to form the copper nanosheet.

16. The method of claim 15, wherein the molar ratio of TOP to Cu-TDA is about 1.8:1 to about 2.8:1.

17. The method of claim 16, wherein the molar ratio of TOP to Cu-TDA is about 2.2:1.

18. The method of claim 15, wherein the purity of the TOP is at least 97%.

19. The method of claim 18, wherein the TOP is substantially free of trioctylphosphine oxide (TOPO).

20. The method of claim 15, wherein the purity of the TOP is at least 90%.

* * * * *